US005502083A

United States Patent [19]

Abe et al.

[11] Patent Number: 5,502,083

[45] Date of Patent: Mar. 26, 1996

[54] ONIUM SALT, PHOTOPOLYMERIZATION INITIATOR, ENERGY RAY-CURING COMPOSITION CONTAINING THE INITIATOR, AND CURED PRODUCT

[75] Inventors: Tetsuya Abe; Kazuhiko Ishii, both of Yono; Minoru Yokoshima, Toride, all of Japan

[73] Assignee: Nippon Kayaku Kabushiki Kaisha, Tokyo, Japan

[21] Appl. No.: 255,469

[22] Filed: Jun. 8, 1994

[51] Int. Cl.⁶ .............................. C08F 2/50; C08F 16/32; C08F 16/22; C08G 59/18

[52] U.S. Cl. .................. 522/31; 522/11; 522/15; 522/25; 522/168; 522/170; 522/173; 522/181; 568/6; 568/15; 568/16; 568/17; 568/34; 568/35; 568/74; 568/75; 568/77

[58] Field of Search .............................. 522/25, 31, 15, 522/11, 170, 181, 168, 173; 568/6, 15, 16, 17, 34, 35, 74, 75, 77

[56] References Cited

U.S. PATENT DOCUMENTS

| | | | |
|---|---|---|---|
| 3,794,576 | 2/1974 | Watt | 204/159.11 |
| 4,161,478 | 7/1979 | Crivello | 260/327 B |
| 4,273,668 | 6/1981 | Crivello | 252/182 |
| 4,374,066 | 2/1983 | Crivello et al. | 260/440 |
| 4,407,759 | 10/1983 | Crivello | 260/440 |
| 4,529,490 | 7/1985 | Crivello et al. | 522/31 |
| 4,684,671 | 8/1987 | Tsuchiya et al. | 568/6 |
| 4,954,416 | 9/1990 | Wright et al. | 522/31 |
| 5,334,699 | 8/1994 | Hsieh | 522/31 |

FOREIGN PATENT DOCUMENTS

| | | |
|---|---|---|
| 0142384 | 5/1985 | European Pat. Off. |
| 3604581 | 8/1987 | Germany |
| 52-14277 | 4/1977 | Japan |
| 52-14278 | 4/1977 | Japan |

Primary Examiner—Susan W. Berman
Attorney, Agent, or Firm—Nields & Lemack

[57] ABSTRACT

The composition of the present invention is excellent in compatibility, transparency and curability and give a cured coat of excellent gloss and of less smell, and cured products of excellent properties can be obtained by curing the composition.

The present invention relates to an onium salt represented by the following formula (1):

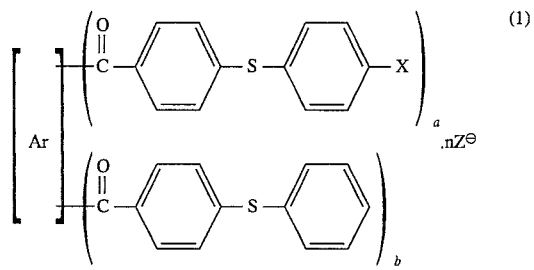

wherein Ar is a mono- to tetra-valent aromatic group, X is a bisphenylsulfonio group which may have a substituent, a is 1–4, b is 0 or 1–3, a+b is 1–4, n is 1–4, and Z is a halide represented by the following formula (3):

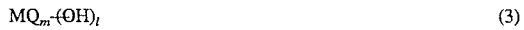

where M is a boron atom, a phosphorus atom, an arsenic atom or an antimony atom, Q is a halogen atom, m is 3–6, l is 0 or 1, and m+l is 4–6; a photopolymerization initiator containing the onium salt as an active ingredient; an energy ray-curable composition containing the initiator; and a cured product.

13 Claims, No Drawings

ONIUM SALT, PHOTOPOLYMERIZATION INITIATOR, ENERGY RAY-CURING COMPOSITION CONTAINING THE INITIATOR, AND CURED PRODUCT

FIELD OF THE INVENTION

The present invention relates to a novel onium salt having a specific structure, a photopolymerization initiator containing the same as an active ingredient, an energy ray-curing composition containing the initiator and curable by irradiation with energy rays, and a cured product.

BACKGROUND OF THE INVENTION

Photopolymerizable compositions have been intensively studied at the request for energy-saving, space-saving and prevention of environmental pollution in the fields of printing inks, paints, coatings, liquid resist inks, etc. and it has been attempted to put them to practical use. However, most of these studies are based on radical polymerization reaction of double bond. Cation polymerizable substances such as epoxy resins are excellent in properties, but are difficult to photopolymerize. Thus, hitherto, such substances having a double bond introduced by acrylic modification have been mainly used.

As a method for curing epoxy resins by exposure to light, for example, U.S. Pat. No. 3794576 proposes to use photosensitive aromatic diazonium salts as a photopolymerization initiator. However, aromatic diazonium salts generate nitrogen gas upon decomposition with light, and if the thickness of epoxy resin coat is more than 15 μ, the coat foams and therefore, the initiator is not suitable for the use of thick coating. Further, the mixture with an epoxy resin gradually cures even in the absence of light and thus has the problem in storage stability and cannot be used as one-pack type compositions.

Various studies have been made in an attempt to solve the defects of the diazonium salt photopolymerization initiators and as a result, aromatic sulfonium salt or aromatic iodonium slat initiators and curable resin compositions containing the same are reported to improve the thick coatability and the storage stability in JP-B-52 14278 and JP-B-52 14277, U.S. Pat. Nos. 4161478 and 4273668. However, the compositions containing these aromatic onium salts are inferior in curability as compared with those containing diazonium salts. Further, aromatic sulfonium salts have the problem in the smell of cured products. For solving these problems, use of aromatic sulfonium salts having a specific group is proposed in U.S. Pat. No. 4374066. However, the problems have not yet been sufficiently solved. Moreover, with expansion of the field where photopolymerizable compositions are used, development of novel photopolymerization initiators and compositions containing the same is important for meeting the market's demand.

SUMMARY OF THE INVENTION

The inventors have conducted an intensive research and as a result, have developed a novel photopolymerization initiator and have succeeded in providing an energy ray-curable composition which is excellent in storage stability, compatibility (especially compatibility between various vinyl ethers and the photopolymerization initiator of the present invention) and curability and which gives cured products having less smell.

That is, the present invention relates to the following onium salts, photopolymerization initiators containing these onium salts as active ingredient, energy ray-curable compositions, and a method for curing the compositions.

(1) An onium salt represented by the following formula (1):

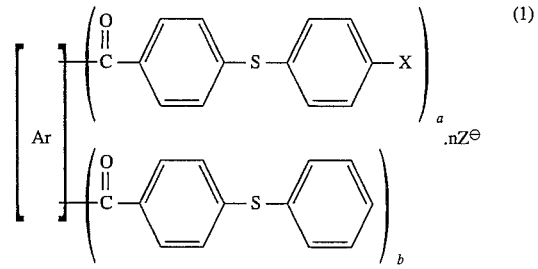

(wherein Ar is a mono-to tetra-valent aromatic group, X is a bisphenylsulfonio group which may have a substituent, a is a number of 1–4, b is 0 or a number of 1–3, a+b is 1–4, n is a number of 1–4, and Z is a halide represented by the following formula (3):

where M is a boron atom, a phosphorus atom, an arsenic atom or an antimony atom, Q is a halogen atom, m is a number of 3–6, l is 0 or 1, and m+l is 4–6).

(2) An onium salt of the above (1) wherein Ar is

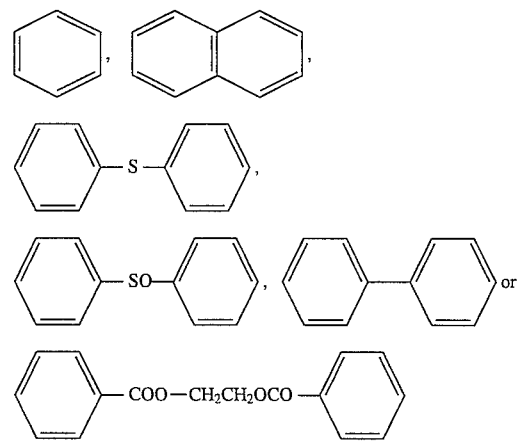

(these aromatic groups may have at least one substituent selected from ($C_1$–$C_5$) alkyl group, ($C_1$–$C_5$) alkyloxycarbonyl group, ($C_1$–$C_5$) alkylcarbonyloxy group, benzoyl group, cyano group, ($C_1$–$C_5$) alkylthio group, and halogen atom); the bisphenylsulfonio group which may have a substituent is a group represented by the following formula (2):

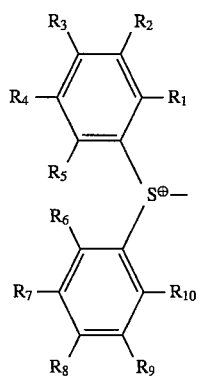 (2)

(wherein $R_1$–$R_{10}$ each is a hydrogen atom, a halogen atom, a nitro group, an alkoxy group, a $C_1$–$C_{25}$ alkyl group, a phenyl group which may have a substituent of $C_6$–$C_{18}$, a phenoxy group, a phenylcarbonyl group, an alkylthio group, a phenylthio group, a benzyloxy group, a $C_1$–$C_{25}$ aliphatic group containing at least one hydroxyl group or a $C_3$–$C_{25}$ aliphatic group containing a group represented by the following formula:

$$-\text{OCH}_2\overset{\overset{\displaystyle R_{11}}{|}}{\text{CHO}}-$$

(where $R_{11}$ is a hydrogen atom or an alkyl group); a is a number of 1–4; b is 0 or a number of 1–3; a+b is 1–4; n is a number of 1–4; and Z is a halide represented by the following formula (3):

$$\text{MQ}_m\text{-(OH)}_l \quad (3)$$

(where M is a boron atom, a phosphorus atom, an arsenic atom or an antimony atom, Q is a halogen atom, m is a number of 3–6, l is 0 or 1, and m+l is 4–6).

(3) An onium salt of the above (2) wherein Ar is

, $R_1$–$R_{10}$ each is a hydrogen atom, a halogen atom, an alkoxy group or a ($C_1$–$C_5$) alkyl group, and M is a phosphorus atom or an antimony atom.

(4) An onium salt of the above (3) wherein at least one of $R_1$–$R_5$ is a halogen atom and the remainder of $R_1$–$R_5$ are hydrogen atoms and at least one of $R_6$–$R_{10}$ is a halogen atom and the remainder of $R_6$–$R_{10}$ are hydrogen atoms.

(5) An onium salt of the above (2) wherein Ar is

, $R_3$ and $R_8$ are halogen atoms, $R_1$, $R_2$, $R_4$–$R_7$, $R_9$ and $R_{10}$ are hydrogen atoms, a is 2, b is 0, n is 2, M is a phosphorus atom or an antimony atom, m is 6, and l is 0.

(6) An onium salt of the above (5) wherein the halogen atom is fluorine atom.

(7) An onium salt represented by the following formula:

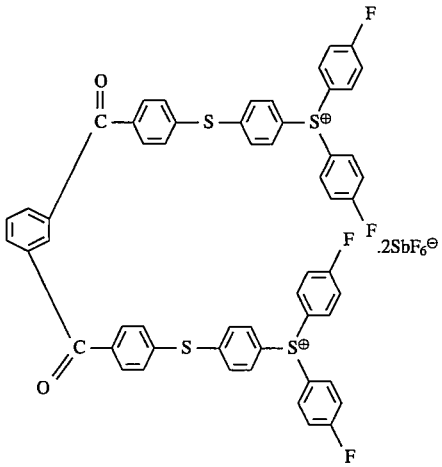

(8) An onium salt represented by the following formula:

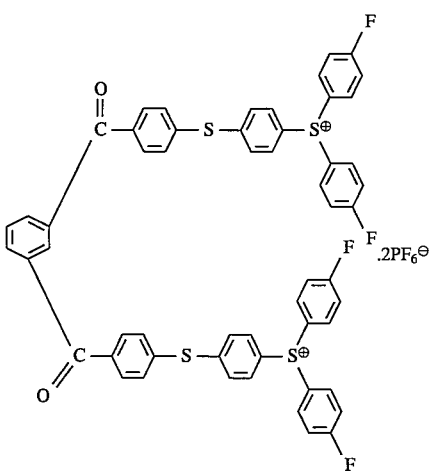

(9) A photopolymerization initiator containing the onium salt of the above (1)–(8) as an active ingredient.

(10) An energy ray-curable composition containing a cation polymerizable substance and the onium salt of the above (1)–(8).

(11) The composition of the above (10) wherein the cation polymerizable substance is an epoxy compound, a vinyl ether compound or a cyclic ether compound.

(12) The composition of the above (11) wherein the epoxy compound is an alicyclic epoxy resin.

(13) The composition of the above (11) wherein the vinyl ether compound is triethylene glycol divinyl ether, tetraethylene glycol divinyl ether, cyclohexane-1,4-dimethyloldivinyl ether, 1,4-butanedioldivinyl ether,

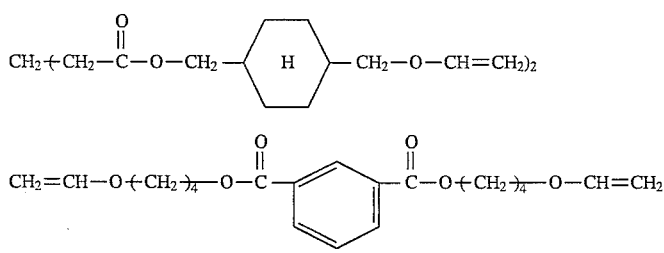

or urethane polyvinyl ether.

(14) The composition of the above (10) wherein the onium salt is the onium salt of the above (7) or (8).

(15) The composition of the above (10) wherein the energy ray is ultraviolet ray.

(16) The composition of the above (10) which comprises 100 parts by weight of the cation polymerizable substance and 0.01–20 parts by weight of the onium salt.

(17) An ultraviolet ray-curable composition which comprises 100 parts by weight of an alicyclic epoxy resin and 0.1–10 parts by weight of the onium salt of the above (7) or (8).

(18) An ultraviolet ray-curable composition which comprises 100 parts by weight of a vinyl ether compound and 0.1–10 parts by weight of the onium salt of the above (7) or (8).

(19) The composition of the above (18) wherein the vinyl ether compound is triethylene glycol divinyl ether, tetraethylene glycol divinyl ether, cyclohexane-1,4-dimethyloldivinyl ether, 1,4-butanedioldivinyl ether,

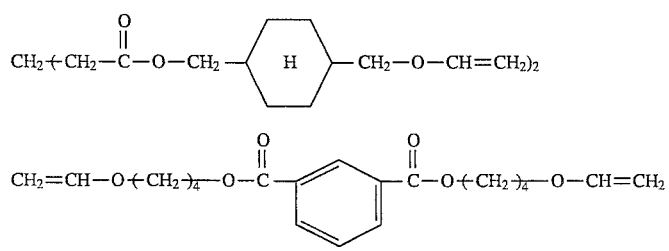

or urethane polyvinyl ether.

(20) A cured product of the composition of the above (10)–(19).

(21) A method for curing the compositions of the above (10)–(19) which comprises irradiating the compositions with ultraviolet ray.

DESCRIPTION OF THE INVENTION

As the mono- to tetra-valent aromatic groups represented by Ar in the formula (1), mention may be made of, for example,

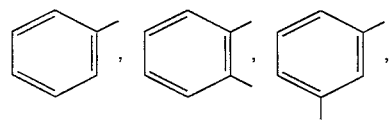

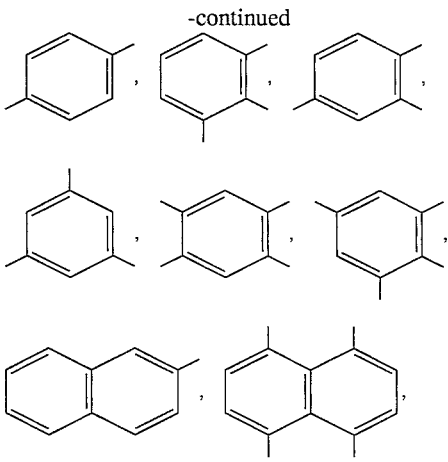

-continued

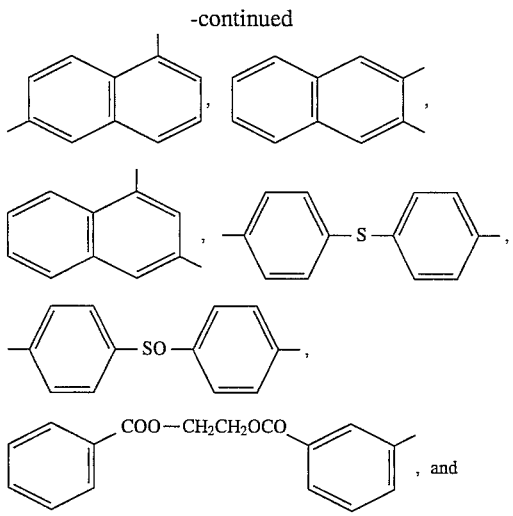

-continued

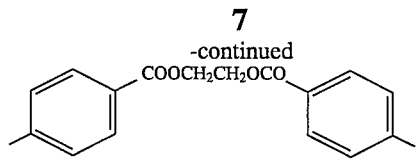

Preferred are divalent groups having the bonds in the meta-position (1,3-position) such as m-phenylene group

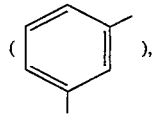

m-naphthylene group

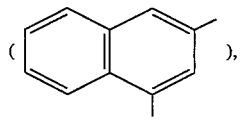

etc.

The mono-to tetra-valent aromatic groups may have at least one substituent, for example, ($C_1$–$C_4$) alkyl groups such as methyl, ethyl, propyl and butyl, ($C_1$–$C_4$) alkylcarbonyloxy groups, halogen atoms such as fluorine, chlorine, bromine and iodine, ($C_1$–$C_4$) alkoxy groups,. benzoyl group, phenyl group, phenylthio group, ($C_1$–$C_4$) alkylthio groups and cyano group.

The bisphenylsulfonio group of X which may have a substituent includes, for example, the group represented by the above formula (2). The halogen atoms of the substituents $R_1$–$R_{10}$ in the formula (2) include F, Cl, Br and I, and F is preferred. The alkoxy groups include, for example, $C_1$–$C_{25}$ alkoxy groups such as methoxy group, ethoxy group, propoxy group, butoxy group, and pentoxy group, and preferred are $C_1$–$C_5$ alkoxy groups. The alkyl groups include, for example, $C_1$–$C_{25}$ alkyl groups such as methyl group, ethyl group, propyl group, and pentyl group, and preferred are $C_1$–$C_5$ alkyl groups. The substituent in the phenyl group which may have a substituent of $C_6$–$C_{18}$ includes $C_6$–$C_{18}$ alkyl groups exemplified by nonyl group and the position of the substituent is preferably the para-position. The alkylthio groups include, for example, $C_1$–$C_5$ alkylthio groups such as methylthio group, ethylthio group, propylthio group, butylthio group, and pentylthio group. The $C_1$–$C_{25}$ aliphatic groups having at least one hydroxyl group include, for example, groups represented by the formula:

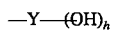

(wherein Y is 0 or S, R is a $C_1$–$C_{25}$ polymethylene such as methylene, dimethylene, trimethylene or tetramethylene or a $C_3$–$C_{10}$ cycloalkylene and R may have a $C_1$–$C_5$ alkyl group such as methyl or ethyl, and h is 1–3). Examples are as follows:

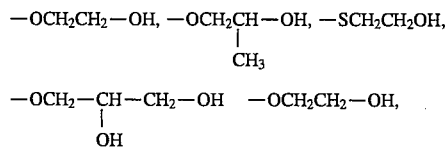

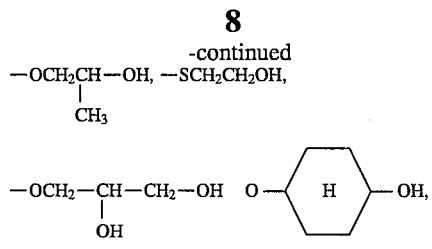

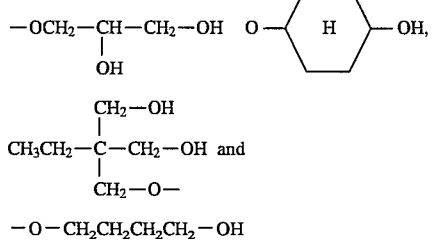

$-O-CH_2CH_2CH_2CH_2-OH$

As examples of $C_3$–$C_{25}$ aliphatic groups containing a group represented by the formula:

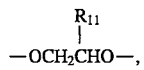

mention may be made of groups represented by the formula:

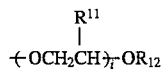

(wherein $R_{12}$ is a hydrogen atom or an alkyl group, i is 2–12, preferably 2–5, and $R_{11}$ is as defined above) such as

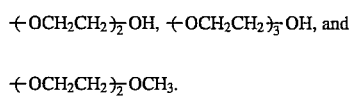

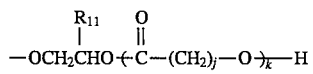

and groups represented by the formula:

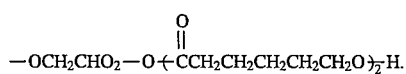

(wherein j is an integer of 1–10, k is 1 or 2, and $R_{11}$ is as defined above) such as $$-OCH_2CHO_2-O{+}CCH_2CH_2CH_2CH_2CH_2O{\overset{\text{O}}{\underset{\|}{}}}_{\overline{2}}H.$$

Examples of $R_{11}$ include $C_1$–$C_5$ alkyl groups such as methyl group, ethyl group, propyl group, butyl group, and pentyl group.

Of these groups, preferred are ① halogen atoms, ② alkyl groups, ③ alkoxy groups, ④ $C_1$–$C_{25}$ aliphatic groups having at least one hydroxyl group, and ⑤ $C_3$–$C_{25}$ aliphatic groups containing a group represented by the formula

Combinations of the substituents $R_1$–$R_{10}$ in the above formula (2) include (a) all of $R_1$–$R_{10}$ being hydrogen atoms, (b) nine to six of $R_1$–$R_{10}$ being hydrogen atoms and one to four of them being groups other than hydrogen atom, (c) three to four of $R_1$–$R_5$ being hydrogen atoms and one to two of them being groups other than hydrogen atom and three to five of $R_6$–$R_{10}$ being hydrogen atoms and zero to two of them being groups other than hydrogen atom, the combination of (c) being preferred one in the combination (b). In more detail, the combination of (c) includes (d) one of $R_1$, $R_2$ and $R_3$, preferably $R_1$ or $R_3$ being the group other than hydrogen atom and the remainder being hydrogen atoms and (e) one or two of $R_1$, $R_2$ and $R_3$ and one or two of $R_6$, $R_7$ and $R_8$ being the groups of the above ①-③ and the remainder being hydrogen atoms. More preferred embodiment in (e) is that $R_3$ and $R_8$ are the groups of the above ①-③, preferably halogen atoms and the remainder are hydrogen atoms.

In the above formula (1), a is preferably 1–2, b is preferably 0 and n is preferably 1–2.

M in the formula (3) used in the formula (1) is preferably a phosphorus atom or an antimony atom, and the halogen atom is preferably fluorine atom. m is preferably 5–6 and l is preferably 0. Preferable examples are $PF_6$ and $SbF_6$.

As the onium salts of the present invention represented by the formula (1), mention may be made of, for example, the following sulfonium salt compounds.

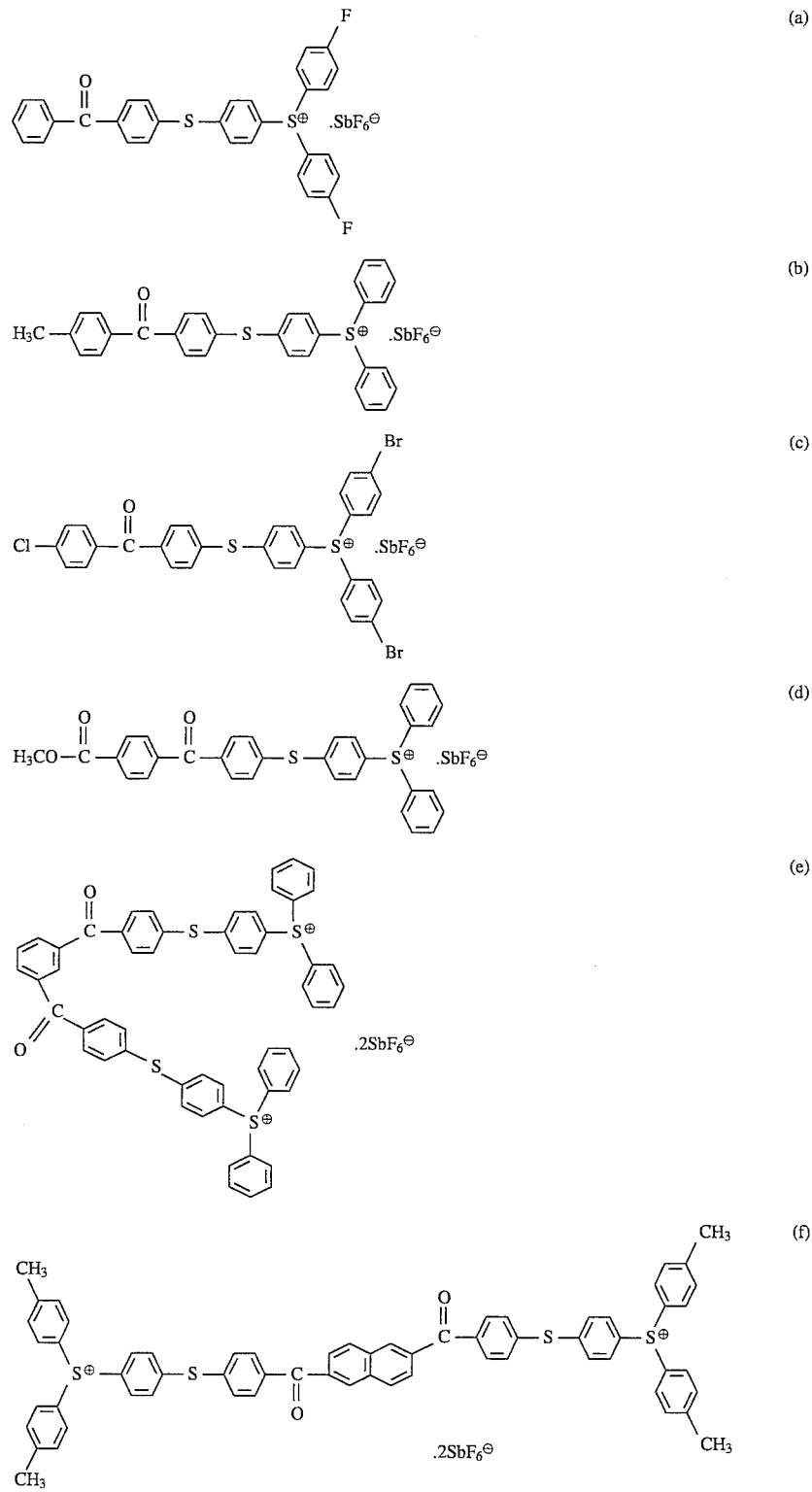

-continued
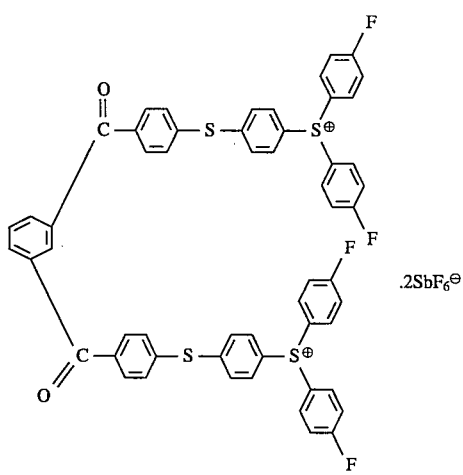
(g)
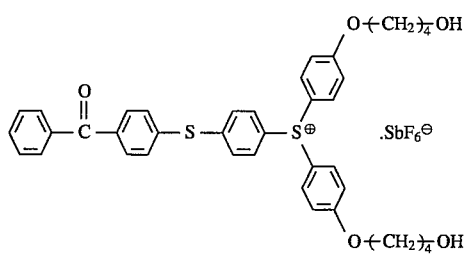
(h)
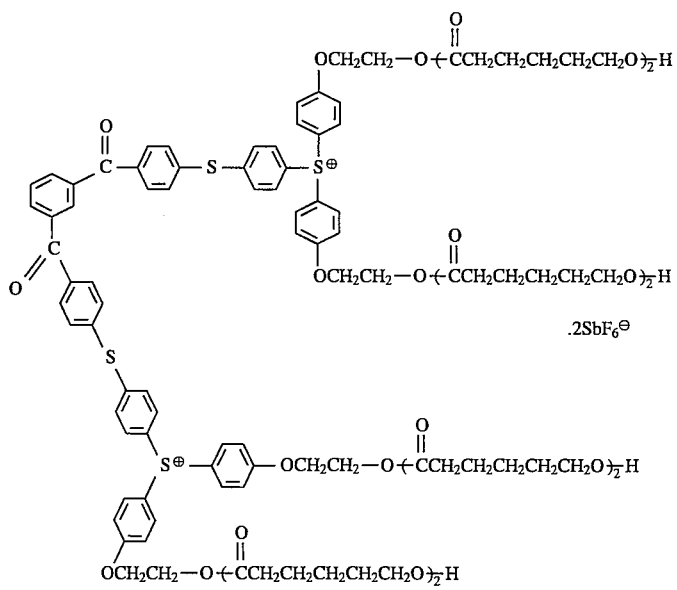
(j)

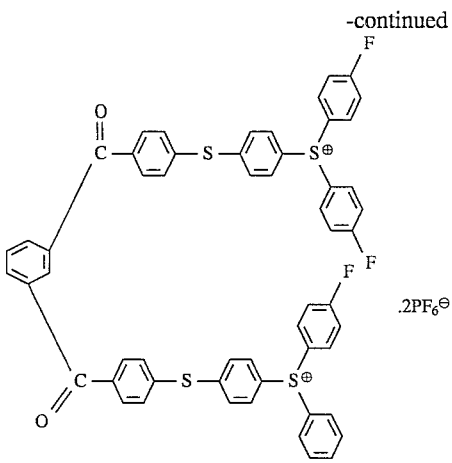

.2PF$_6^{\ominus}$

The onium salts of the present invention can be synthesized by the following process (1) or (2).

The process (1): The onium salts are prepared by the known reaction for preparation of sulfonium salts using as starting materials a diphenyl sulfide compound represented by the following formula (5):

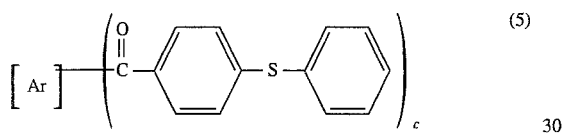

(5)

(wherein Ar and c are as defined above) and a substituted or unsubstituted diphenyl sulfoxide compound represented by the following formula (4):

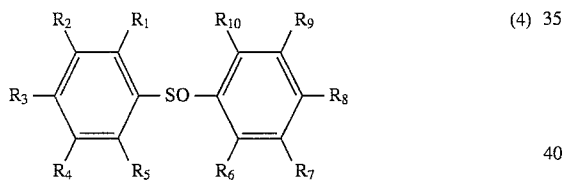

(4)

(wherein $R_1$–$R_{10}$ are as defined above).

The process (2): The onium salts are prepared by previously preparing a corresponding substituted or unsubstituted sulfonium salt and then converting or introducing the substituent.

The process (1) is explained in detail.

A diphenyl sulfide compound represented by the formula (5) is subjected to condensation reaction with a substituted or unsubstituted diphenyl sulfoxide compound represented by the formula (4) in an amount of preferably 0.25–1.2 mol, more preferably 1.0–1.1 mol based on 1 equivalent of the terminal sulfide group of the former compound in the known manner, for example, at room temperature to 150° C. in a dehydrating agent (for example, phosphorus pentoxide, concentrated sulfuric acid, acetic anhydride or the like) and then, the reaction mixture is added dropwise to an aqueous solution of a compound represented by the following formula (3'):

B—MQ$_m$—(OH)$_l$ (3')

(wherein B is an alkali metal and M, Q, m and l are as defined above).

Examples of the compound represented by the formula (5) are shown below.

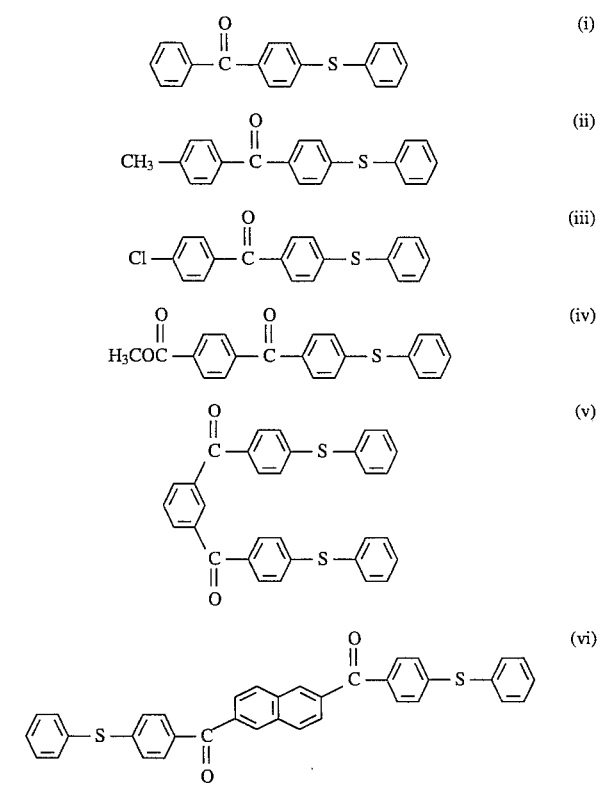

As examples of the compound represented by the formula (4), mention may be made of diphenyl sulfoxide, 4,4'-difluorodiphenyl sulfoxide, 2,2'-difluorodiphenyl sulfoxide, 3,3'-difluorodiphenyl sulfoxide, 4,2'-difluorodiphenyl sulfoxide, 4,4'-dibromodiphenyl sulfoxide, 4,4'-dichlorodiphenyl sulfoxide, 2,2'-dichlorodiphenyl sulfoxide, 2,2', 4,4'-tetrachlorodiphenyl sulfoxide, 4,4'-dimethyldiphenyl sulfoxide, 4,4'-diethyldiphenyl sulfoxide, 4,4'-dimethoxydiphenyl sulfoxide, 4-methylthiodiphenyl sulfoxide, 4-phenylthiodiphenyl sulfoxide, 4-phenylcarbonyldiphenyl sulfoxide, 4-bemzyloxydiphenyl sulfoxide, 2-nitrodiphenyl sulfoxide, 4-phenyldiphenyl sulfoxide, 4-(p-nonylphenyl)diphenyl sulfoxide, and 4-phenyloxydiphenyl sulfoxide.

In the above formula (3'), B is an alkali metal such as Na or K. Examples of the compound represented by the formula (3') are NaSbF$_6$, NaPf$_6$, NaAsf$_6$, NaBF$_4$, NaSbF$_5$OH, KSbF$_6$, KPf$_6$, KAsf$_6$, and KSbF$_5$OH.

The compound represented by the formula (5) can be obtained by reacting an aromatic carboxylic acid compound with diphenyl sulfide. As a reaction solvent, preferred is a solution prepared by dissolving phosphoric anhydride in an alkylsulfonic acid such as methanesulfonic acid. Reaction temperature is preferably from room temperature to 130° C. Reaction time is preferably 0.5–15 hours. The proportion of the aromatic carboxylic acid compound and the diphenyl sulfide is preferably about 1 mol of diphenyl sulfide for 1 equivalent of the carboxylic acid in the aromatic carboxylic acid compound.

Examples of the aromatic carboxylic acid compound are the following mono- or polycarboxylic acids.

Aromatic monocarboxylic acids such as benzoic acid, o-methylbenzoic acid, m-methylbenzoic acid, p-methylbenzoic acid, 3,5-dimethylbenzoic acid, p-ethylbenzoic acid, p-butylbenzoic acid, o-methylcarbonyloxybenzoic acid, p-methyloxycarbonylbenzoic acid, o-chlorobenzoic acid, m-chlorobenzoic acid, p-chlorobenzoic acid, 2,4-dichlorobenzoic acid, o-fluorobenzoic acid, m-fluorobenzoic acid, 2,4-difluorobenzoic acid, p-methoxybenzoic acid, o-benzoylbenzoic acid, p-phenylbenzoic acid, napthalene-2-carboxylic acid, p-phenylthiobenzoic acid, o-cyanobenzoic acid, p-cyanobenzoic acid, p-methylthiobenzoic acid, and aromatic polycarboxylic acids such as isophthalic acid, terephthalic acid, benzene-1,2,4-tricarboxylic acid, naphthalene-1,4,5,8-tetracarboxylic acid, naphthalene-2,6-di-carboxylic acid, naphthalene-2,3-dicarboxylic acid,

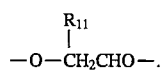

This process may be carried out by reacting a sulfonium salt synthesized by the process (1), for example, a halide compound such as one represented by the following formula (6):

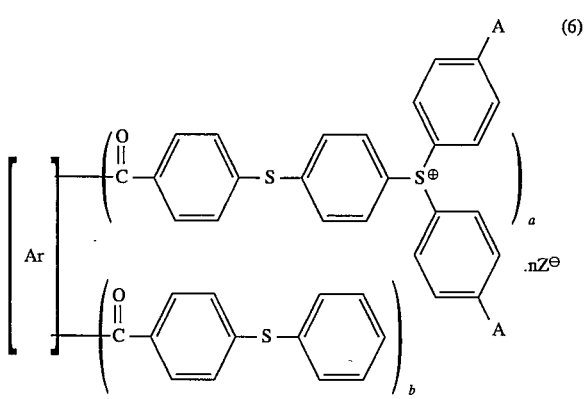

(wherein A is a halogen atom and Ar, a, b, n and Z are as defined above) with an alcohol by the known process, for example, at room temperature to 150° C. in the presence of a basic compound (for example, sodium hydroxide or potassium hydroxide).

Examples of the alcohols are methanol, ethanol, carbitol, ethylene glycol, polyethylene glycol, propylene glycol, glycerin, trimethylolpropane, 1,4-butanediol, cyclohexanediol, and monohydroxyethylthiol. By this process (2), there can be obtained onium salts in which the halide portion in the above-mentioned halide is converted to a substituent such as

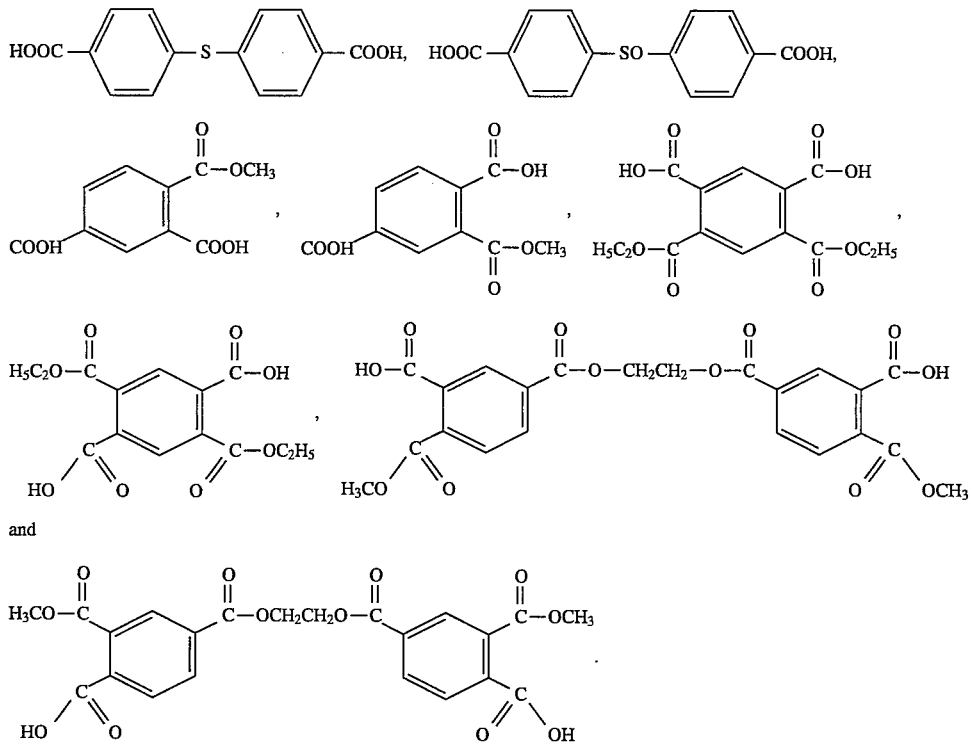

Next, the process (2) is explained in detail.

The process (2) is suitable for preparation of a compound represented by the formula (1) wherein at least one of $R_1$–$R_{10}$ in the formula (2) is an alkoxy group, a $C_1$–$C_{25}$ aliphatic group having at least one hydroxyl group or a $C_3$–$C_{25}$ aliphatic group containing the group represented by the formula:

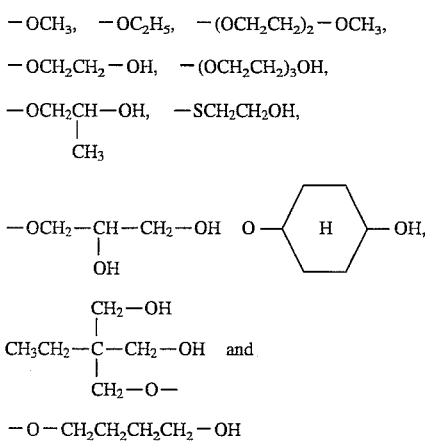

—O—CH₂CH₂CH₂CH₂—OH

The present invention further includes onium salts obtained by further reacting a hydroxyl group of the compounds obtained by the process (2) in which the substituent

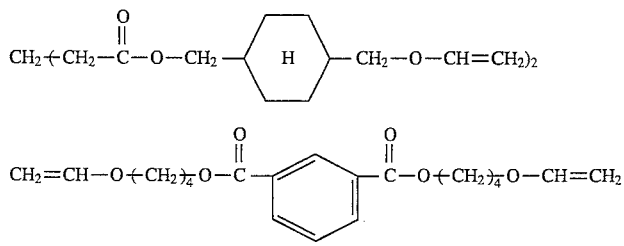

has been converted to a substituent having the hydroxyl group with lactones (for example, ε-caprolactone) or acids (for example, acetic acid and acetic anhydride) by known process.

Next, the energy ray-curable composition of the present invention will be explained below.

The cation polymerizable substances used in the composition include, for example, cation polymerizable vinyl ether compounds such as epoxy compounds, styrene and vinyl ether and cyclic ether compounds, preferably spiro cyclic ether compounds such as spiro-orthoesters, bicyclo-orthoesters and spiro-orthocarbonates.

The epoxy compounds include, for example, conventionally known aromatic epoxy resins, alicyclic epoxy resins, aliphatic epoxy resins and furthermore, epoxide monomers and episulfide monomers.

Examples of the aromatic epoxy resins are polyglycidyl ethers of polyhydric phenols having at least one aromatic nucleus or alkylene oxide adducts thereof, for example, glycidyl ethers produced by the reaction of bisphenol compounds such as bisphenol A, bisphenol F and bisphenol S or alkylene oxide (such as ethylene oxide, propylene oxide or butylene oxide) adducts of these bisphenol compounds with epichlorohydrin, novolak type epoxy resins (such as phenol.novolak type epoxy resins, cresol.novolak type epoxy resins and brominated phenol.novolak type epoxy resins) and trisphenolmethane triglycidyl ether.

Examples of the alicyclic epoxy resins are 3,4-epoxycyclohexylmethyl-3,4-epoxycyclohexane carboxylate, bis-(3, 4-epoxycyclohexylmethyl) adipate, 2-(3,4-epoxycyclohexyl-5,5-spiro- 3,4-epoxy)cyclohexanone-m-dioxane, bis(2,3-epoxycyclopentyl) ether and EHPE-3150 (alicyclic epoxy resin having a softening point of 71° C. manufactured by Daicel Ltd.).

Examples of the aliphatic epoxy resins are polyglycidyl ethers of aliphatic polyhydric alcohols or alkylene oxide adducts thereof. Representative examples thereof are diglycidyl ether of 1,4-butanediol, diglycidyl ether of 1,6-hexanediol, triglycidyl ether of glycerin, triglycidyl ether of trimethylolpropane, diglycidyl ether of polyethylene glycol, diglycidyl ether of propylene glycol, and polyglycidyl ethers of polyether polyols obtained by adding at least one alkylene oxide (such as ethylene oxide and propylene oxide) to aliphatic polyhydric alcohols such as ethylene glycol, propylene glycol and glycerin.

Examples of the epoxide monomers are monoglycidyl ethers of aliphatic higher alcohols and monoglycidyl ethers of phenol, cresol, or butylphenol or polyether alcohols obtained by adding thereto alkylene oxides.

The cation polymerizable vinyl ether compounds include, for example, triethylene glycol divinyl ether, tetraethylene glycol divinyl ether, cyclohexane-1,4-dimethylolvinyl ether, 1,4-butanedioldivinyl ether, and urethane polyvinyl ethers (such as VECtomer 2010 manufactured by Allied-Signal Co., Ltd.).

These cation polymerizable substances are used each alone or in admixture of two or more.

The curable composition of the present invention comprises, as essential components, 100 parts by weight of the cation polymerizable substance and 0.01–20 parts by weight, more preferably 0.1–10 parts by weight of the photopolymerization initiator containing the onium salt represented by the formula (1) as an active ingredient. Specific proportion of these components is determined depending on various factors such as properties of the cation polymerizable substance, kind of the energy rays, irradiation amount of the energy rays, and the desired curing time, temperature and humidity, and thickness of coat. In order to make it easy to dissolve the photopolymerization initiator in the cation polymerizable substance, the photopolymerization initiator may be previously dissolved in a solvent (such as propylene carbonate, carbitol, carbitol acetate or γ-butyrolactone).

The curable composition of the present invention can be prepared by the methods such as mixing, dissolution and kneading of the cation polymerizable substance and the photopolymerization initiator.

The curable composition of the present invention can be cured to the state of set to touch or the state insoluble in solvents by irradiation with energy rays such as ultraviolet rays for 0.1 second—several minutes. Suitable energy rays may be any of those which have an energy capable of inducing the decomposition of the photopolymerization initiator. Preferably usable are electromagnetic wave energy having a wavelength of 2000–7000 angstrom obtained from high or low pressure mercury lamp, xenon lamp, sterilization lamp, laser or the like and high-energy rays such as electron ray, X-ray, and radiation. Ultraviolet ray is preferred. Exposure to the energy ray is usually conducted for about 0.1–10 seconds which is sufficient although it depends on the intensity of the energy ray. However, for relatively thick coat, it is preferred to take more time for the exposure. In 0.1 second—several minutes after irradiation with energy rays, most of the compositions is dried to the state of set to touch due to cationic polymerization, but in some case, it is preferred to carry out heating for acceleration of the cationic polymerization reaction.

So long as the cationic polymerization is not hindered, the composition of the present invention may further contain solvents for dilution and, for modification, unreactive resins and (meth)acrylate ester compounds (for example, oligomers such as epoxy (meth)acrylates which are reaction products of epoxy resins such as bisphenol A type epoxy resin and novolak type epoxy resin with (meth)acrylic acids, urethane (meth)acrylates, and polyester poly(meth)acrylates and monomers such as 2-hydroxy(meth)acrylates, 1,6-hexanediol di(meth)acrylates, 1,9-nonanediol di(meth)acrylates, trimethylolpropane tri(meth)acrylates and pentaerythritol tri(meth)acrylates). When the (meth)acrylate ester compound is used, it is preferred to use together a photo-radical polymerization initiator such as 1-hydroxycyclohexylphenyl ketone, acetophenon dimethylketal or benzoylmethyl ether. Furthermore, organic carboxylic acids or acid anhydrides may be used for improving electrical characteristics or polyols and other flexible prepolymers may be added for imparting rubber elasticity.

The composition of the present invention is mainly coated on the surface of articles at a thickness of, for example, 1–200 μm, preferably 3–50 μm and is generally used in the form of a trasparent liquid. For some uses, inert pigments, dyes, fillers, antistatic agents, flame retarders, antifoamers, flowability adjusters, sensitizers, accelerators, light stabilizers and others may be added to the composition. The composition of the present invention can be applied to articles of metals, woods, rubbers, plastics, glasses, ceramics, etc. Further specific uses of the present invention include paint, coating, ink, resist, liquid resist, adhesive, molding materials, casting materials, putty, glass fiber impregnant, sealer, etc.

The present invention will be explained by the following examples. All parts in the examples and synthesis examples are by weight.

Synthesis examples of diphenyl sulfide compounds represented by the formula (5)

SYNTHESIS EXAMPLE 1

(Synthesis of the compound represented by the formula (i))

16.2 parts of phosphorus pentoxide was completely dissolved in 161.7 parts of methanesulfonic acid. Then, in the solution were charged 18.6 parts of diphenyl sulfide and 12.2 parts of benzoic acid and the reaction was carried out for 1 hour at 80° C. and the completion of the reaction was confirmed by liquid chromatography. The reaction mixture was added dropwise to 1000 parts of aqueous potassium hydroxide solution (prepared by dissolving 200 parts of potassium hydroxide in 800 parts of water) and the resulting precipitate was collected by filtration, dried, then dissolved in 400 parts of ethanol with heating (60° C.), and cooled to 5° C. The precipitate was collected by filtration and dried to obtain 20.3 parts of a white solid (i). The product had a melting point of 69–70° C.

SYNTHESIS EXAMPLE 2

(Synthesis of the compound represented by the formula (ii))

18.3 parts of phosphorus pentoxide was completely dissolved in 180.3 parts of methanesulfonic acid. Then, in the solution were charged 18.6 parts of diphenyl sulfide and 13.6 parts of p-methylbenzoic acid and the reaction was carried out for 1 hour at 80° C. The completion of the reaction was confirmed by liquid chromatography. The reaction mixture was treated in the same manner as in Synthesis Example 1 to obtain 20.2 parts of a white solid (ii). The product had a melting point of 117°–118° C.

SYNTHESIS EXAMPLE 3

(Synthesis of the compound represented by the formula (iii))

20.8 parts of phosphorus pentoxide was completely dissolved in 208.2 parts of methanesulfonic acid. Then, in the solution were charged 18.6 parts of diphenyl sulfide and 15.7 parts of p-chlorobenzoic acid and the reaction was carried out for 1 hour at 80° C. The completion of the reaction was confirmed by liquid chromatography. The reaction mixture was treated in the same manner as in Synthesis Example 1 to obtain 21.6 parts of a white solid (iii). The product had a melting point of 134°–135° C.

SYNTHESIS EXAMPLE 4

(Synthesis of the compound represented by the formula (iv))

23.9 parts of phosphorus pentoxide was completely dissolved in 238.6 parts of methanesulfonic acid. Then, in the solution were charged 18.6 parts of diphenyl sulfide and 18.0 parts of p-methyloxy-carbonylbenzoic acid and the reaction was carried out at 80° C. for 1 hour. The completion of the reaction was confirmed by liquid chromatography. The reaction mixture was treated in the same manner as in Synthesis Example 1 to obtain 21.6 parts of a white solid (iv). The product had a melting point of 145°–148° C.

SYNTHESIS EXAMPLE 5

(Synthesis of the compound represented by the formula (v))

22.0 parts of phosphorus pentoxide was completely dissolved in 220.1 parts of methanesulfonic acid. Then, therein were charged 37.2 parts of diphenyl sulfide and 16.6 parts of isophthalic acid and the reaction was carried out for 6 hours at 80° C. The completion of the reaction was confirmed by liquid chromatography. The reaction mixture was treated in the same manner as in Synthesis Example 1 to obtain 35.2 parts of a white solid (v). The product had a melting point of 147°–152° C.

SYNTHESIS EXAMPLE 6

(Synthesis of the compound represented by the formula (vi))

28.6 parts of phosphorus pentoxide was completely dissolved in 286.4 parts of methanesulfonic acid. Then, in the solution were charged 37.2 parts of diphenyl sulfide and 21.6 parts of naphthalene-2,6-dicarboxylic acid and the reaction was carried out at 80° C. for 6 hours. The completion of the reaction was confirmed by liquid chromatography. The reaction mixture was treated in the same manner as in Synthesis Example 1 to obtain 37.0 parts of a white solid (vi). The product had a melting point of 195°–200° C.

Synthesis of onium salts represented by the formula (1):

EXAMPLE 1

(Synthesis of compound (a))

29.0 parts of the compound (4-benzoyl-diphenyl sulfide) obtained in Synthesis Example 1, 23.9 parts of 4,4'-difluorodiphenyl sulfoxide, 39.8 parts of phosphorus pentoxide and 398 parts of methanesulfonic acid as a solvent were charged and heated to 80° C., and the reaction was carried out for 3 hours with stirring. With stirring, the reaction mixture was gradually added dropwise to 280.0 parts of an aqueous solution of NaPF6 (prepared by dissolving 16.8 parts of $NaPF_6$ in 263.2 parts of water) at 5° C. The precipitated white solid was filtrated, dried and dissolved in 650 parts of isopropanol with heating (70° C.). The solution was cooled to 0° C. and filtrated and dried to obtain 46.0 parts of a white solid (compound (a)). The product had a melting point of 131°–139° C. The results of elemental analysis are nearly the same as the calculated values.

| Element | Found (wt %) | Calcd. (wt %) |
| --- | --- | --- |
| C | 56.72 | 56.71 |
| H | 3.24 | 3.22 |
| S | 9.79 | 9.77 |
| P | 4.75 | 4.72 |
| F | 23.17 | 23.15 |

EXAMPLE 2

(Synthesis of compound (b))

30.4 parts of the compound (4-(p-methylbenzoyl)-diphenyl sulfide) obtained in Synthesis Example 2, 20.2 parts of diphenyl sulfoxide, and 179.8 parts of concentrated sulfuric acid were charged and the reaction was carried out at room temperature for 24 hours. With stirring, the reaction mixture was gradually added dropwise to 431.1 parts of an aqueous solution of $NaSbF_6$ (prepared by dissolving 25.8 parts of $NaSbF_6$ in 405.3 parts of water) at 5° C. The precipitated white solid was filtrated, dried and dissolved in 650 parts of isopropanol with heating (70° C). The solution was cooled to 0° C. and filtrated and dried to obtain 50.8 parts of a white solid (compound (b)). The product had a melting point of 110°–118° C. The results of elemental analysis were nearly the same as the calculated values.

| Element | Found (wt %) | Calcd. (wt %) |
| --- | --- | --- |
| C | 52.98 | 52.99 |
| H | 3.48 | 3.47 |
| S | 8.85 | 8.84 |
| Sb | 16.80 | 16.78 |
| F | 15.73 | 15.71 |

EXAMPLE 3

(Synthesis of compound (c))

32.5 parts of the compound (4-(p-chlorobenzoyl)-diphenyl sulfide) obtained in Synthesis Example 3, 36 parts of 4,4'-dibromo.diphenyl sulfoxide, and 240.6 parts of concentrated sulfuric acid were charged and the reaction was carried out at room temperature for 24 hours. With stirring, the reaction mixture was gradually added dropwise to 431.1 parts of an aqueous solution of $NaSbF_6$ (prepared by dissolving 25.8 parts of $NaSbF_6$ in 405.3 parts of water) at 5° C. The precipitated white solid was filtrated, dried and dissolved in 650 parts of isopropanol with heating (70° C.). The solution was cooled to 0° C. and filtrated and the residue was dried to obtain 63.3 parts of a white solid (compound (c)). The product had a melting point of 125°–129° C. The results of elemental analysis were nearly the same as the calculated values.

| Element | Found (wt %) | Calcd. (wt %) |
| --- | --- | --- |
| C | 41.22 | 41.21 |
| H | 2.24 | 2.23 |
| S | 7.10 | 7.10 |
| Cl | 3.93 | 3.92 |
| Br | 17.72 | 17.69 |
| Sb | 13.49 | 13.47 |
| F | 12.65 | 12.62 |

EXAMPLE 4

(Synthesis of compound (d))

34.8 parts of the compound obtained in Synthesis Example 4, 20.2 parts of diphenyl sulfoxide and 173.1 parts of concentrated sulfuric acid were charged and the reaction was carried out at room temperature for 24 hours. With stirring, the reaction mixture was gradually added dropwise to 431.1 parts of an aqueous solution of $NaSbF_6$ (prepared by dissolving 26.8 parts of $NaSbF_6$ in 405.3 parts of water) at 0° C. The precipitated white solid was filtrated, dried and dissolved in 650 parts of isopropanol with heating (70° C.). The solution was cooled to 0° C. and filtrated and the residue was dried to obtain 53.9 parts of a white waxy product (compound (d)). The results of elemental analysis were nearly the same as the calculated values.

| Element | Found (wt %) | Calcd. (wt %) |
| --- | --- | --- |
| C | 51.54 | 51.52 |
| H | 3.30 | 3.28 |
| S | 8.35 | 8.33 |
| Sb | 15.83 | 15.82 |
| F | 14.84 | 14.82 |

EXAMPLE 5

(Synthesis of compound (e))

50.3 parts of the compound obtained in Synthesis Example 5, 40.4 parts of diphenyl sulfoxide and 208.1 parts of concentrated sulfuric acid were charged and the reaction was carried out at room temperature for 24 hours. With stirring, the reaction mixture was gradually added dropwise to 862.3 parts of an aqueous solution of $NaSbF_6$ (prepared by dissolving 51.7 parts of $NaSbF_6$ in 810.6 parts of water) at room temperature. The precipitated white solid was filtrated, dried and dissolved in 650 parts of isopropanol with heating (70° C.). The solution was cooled to 0° C. and filtrated and the residue was dried to obtain 94.1 parts of a white solid (compound (e)). The product had a melting point of 152°–162° C. The results of elemental analysis were nearly the same as the calculated values.

| Element | Found (wt %) | Calcd. (wt %) |
|---|---|---|
| C | 50.05 | 50.03 |
| H | 3.02 | 3.00 |
| S | 9.57 | 9.54 |
| Sb | 18.11 | 18.10 |
| F | 16.99 | 16.96 |

EXAMPLE 6

(Synthesis of compound (f))

55.3 parts of the compound obtained in Synthesis Example 6, 46.1 parts of 4,4'-dimethyldiphenyl sulfoxide and 233.4 parts of concentrated sulfuric acid were charged and the reaction was carried out at room temperature for 24 hours. With stirring, the reaction mixture was gradually added dropwise to 862.3 parts of an aqueous solution of $NaSbF_6$ (prepared by dissolving 51.7 parts of $NaSbF_6$ in 810.6 parts of water) at room temperature. The precipitated white solid was filtrated, dried and dissolved in 650 parts of isopropanol with heating (70° C.). The solution was cooled to 0° C. and filtrated and the residue was dried to obtain 96.5 parts of a white solid (compound (f)). The product had a melting point of 201°–205° C. The results of elemental analysis were nearly the same as the calculated values.

| Element | Found (wt %) | Calcd. (wt %) |
|---|---|---|
| C | 52.23 | 52.20 |
| H | 3.55 | 3.53 |
| S | 8.98 | 8.97 |
| Sb | 17.09 | 17.06 |
| F | 15.99 | 15.98 |

EXAMPLE 7

(Synthesis of compound (g))

50.3 parts of the compound obtained in Synthesis Example 5, 47.6 parts of 4,4'-difluorodiphenyl sulfoxide and 225.4 parts of concentrated sulfuric acid were charged and the reaction was carried out at room temperature for 24 hours. With stirring, the reaction mixture was gradually added dropwise to 862.3 parts of an aqueous solution of $NaSbF_6$ (prepared by dissolving 51.7 parts of $NaSbF_6$ in 810.6 parts of water) at room temperature. The precipitated white solid was filtrated, dried and dissolved in 650 parts of isopropanol with heating (70° C.). The solution was cooled to 0° C. and filtrated and the residue was dried to obtain 94.1 parts of a white solid (compound (g)). The product had a melting point of 163°–172° C. The results of elemental analysis were nearly the same as the calculated values.

| Element | Found (wt %) | Calcd. (wt %) |
|---|---|---|
| C | 47.51 | 47.48 |
| H | 2.58 | 2.56 |
| S | 9.07 | 9.05 |
| Sb | 17.20 | 17.18 |
| F | 21.40 | 21.46 |

EXAMPLE 8

(Synthesis of compound (h))

32.8 parts of the compound obtained in Example 1, 4.0 parts of sodium hydroxide and 100 parts of 1,4-butanediol were charged and the reaction was carried out at room temperature for 24 hours. Then, the reaction mixture was poured into water and the resulting oily substance was separated and dried to obtain 41.8 parts of a light yellow liquid product (compound (h)). The results of elemental analysis were nearly the same as the calculated values.

| Element | Found (wt %) | Calcd. (wt %) |
|---|---|---|
| C | 52.80 | 52.78 |
| H | 4.45 | 4.43 |
| S | 7.23 | 7.22 |
| Sb | 13.70 | 13.71 |
| F | 12.85 | 12.84 |

EXAMPLE 9

(Synthesis of compound (j))

70.8 parts of the compound obtained in Example 7, 4.0 parts of sodium hydroxide and 200 parts of ethylene glycol were charged and the reaction was carried out at room temperature for 24 hours. Then, the reaction mixture was poured into water and the precipitated white solid was filtrated and dried to obtain a product which was solid at room temperature. Then, 78.2 parts of the product, 48.5 parts of $\epsilon$-caprolactone and 0.04 part of stannous chloride were charged and the reaction was carried out at 120° C. for 15 hours. When it was confirmed that content of $\epsilon$-caprolactone in the reaction mixture was 1% or less, the reaction was completed to obtain 126.7 parts of a liquid product (compound (j)). The results of elemental analysis were nearly the same as the calculated values.

| Element | Found (wt %) | Calcd. (wt %) |
|---|---|---|
| C | 53.86 | 53.84 |
| H | 5.48 | 5.49 |
| S | 5.15 | 5.13 |
| Sb | 9.76 | 9.75 |
| F | 9.13 | 9.13 |

EXAMPLE 10

(Synthesis of compound (k))

50.3 parts of the compound obtained in Synthesis Example 5, 47.6 parts of 4,4'-difluorodiphenyl sulfoxide and 225.4 parts of concentrated sulfuric acid were charged and the reaction was carried out at room temperature for 24 hours. With stirring, the reaction mixture was gradually added dropwise to 559.8 parts of an aqueous solution of NaPF6 (prepared by dissolving 33.6 parts of $NaPF_6$ in 5.62 parts of water) at room temperature. The precipitated white solid was filtrated, dried and dissolved in 650 parts of isopropanol with heating (70° C.). The solution was cooled to 0° C. and filtrated and the residue was dried to obtain 104.9 parts of a white solid (compound (k)). The product had a melting point of 154°–163° C. The results of elemental analysis were nearly the same as the calculated values.

| Element | Found (wt %) | Calcd. (wt %) |
|---------|--------------|---------------|
| C | 54.48 | 54.46 |
| H | 2.97 | 2.94 |
| S | 10.35 | 10.38 |
| P | 5.01 | 5.02 |
| F | 24.59 | 24.61 |

EXAMPLES 11–30 AND COMPARATIVE EXAMPLES 1–6

(Experiments on compositions)

Energy ray-curable compositions were prepared by mixing and dissolving the components as shown in Table 1 and Table 2. Each of the compositions was coated on an aluminum test panel at a thickness of 5 μ and irradiated with ultraviolet ray by a high pressure mercury lamp (80 W/cm) provided at a distance of 8 cm from the coat, whereby the coat was cured. The prepared composition was tested on transparency, storage stability, set to touch, gloss of cured coat and smell. The results are shown in Table 1 and Table 2.

Test methods:

Transparency: Transparency of the composition was visually evaluated.

○- - - Completely transparent.

Δ- - - Slightly hazed.

X - - - Hazed.

XX - - - Immediately separated into components.

Storage stability: The composition was stored for 3 months at 40° C. and stability was examined.

○- - - No change.

Δ- - - Somewhat tacky.

X - - - Gelled.

Set to touch: This was determined by measuring the irradiation quantity (mJ/cm$^2$) required for the coat reaching the state of set to touch.

Gloss: The coat was irradiated with ultraviolet ray in a quantity (mJ/cm$^2$) required for the coat reaching the state of set to touch and then, the surface of the cured coat was visually evaluated.

○- - - Good gloss.

Δ- - - Somewhat cloudy.

X - - - No gloss.

Smell: The surface of the coat was irradiated with 1000 mJ/cm$^2$ of ultraviolet ray and the smell of the surface of the cured coat was examined.

○- - - No smell.

Δ- - - Slight smell.

X - - - Considerable smell.

XX - - - Strong smell.

TABLE 1

|  | Example |  |  |  |  |  |  |  |  |  | Comparative Example |  |  |
|---|---|---|---|---|---|---|---|---|---|---|---|---|---|
|  | 11 | 12 | 13 | 14 | 15 | 16 | 17 | 18 | 19 | 20 | 1 | 2 | 3 |
| Photopolymerization initiator: | | | | | | | | | | | | | |
| obtained in Example 1 | 1.5 | | | | | | | | | | | | |
| obtained in Example 2 | | 1.5 | | | | | | | | | | | |
| obtained in Example 3 | | | 1.5 | | | | | | | | | | |
| obtained in Example 4 | | | | 1.5 | | | | | | | | | |
| obtained in Example 5 | | | | | 1.5 | | | | | | | | |
| obtained in Example 6 | | | | | | 1.5 | | | | | | | |
| obtained in Example 7 | | | | | | | 1.5 | | | | | | |
| obtained in Example 8 | | | | | | | | 1.5 | | | | | |
| obtained in Example 9 | | | | | | | | | 1.5 | | | | |
| obtained in Example 10 | | | | | | | | | | 1.5 | | | |
| Compound 1 (*1) | | | | | | | | | | | 1.5 | | |
| Compound 2 (*2) | | | | | | | | | | | | 1.5 | |
| Compound 3 (*3) | | | | | | | | | | | | | 1.5 |
| Epoxyresin: | | | | | | | | | | | | | |
| Celloxide 2021 (*4) | 80 | 80 | 80 | 80 | 80 | 80 | 80 | 80 | 80 | 80 | 80 | 80 | 80 |
| EHPE-3150 (*5) | 20 | 20 | 20 | 20 | 20 | 20 | 20 | 20 | 20 | 20 | 20 | 20 | 20 |
| Transparency | ○ | ○ | ○ | ○ | ○ | ○ | ○ | ○ | ○ | ○ | ○ | ○ | ○ |
| Storage stability | ○ | ○ | ○ | ○ | ○ | ○ | ○ | ○ | ○ | ○ | ○ | ○ | ○ |
| Set to tough (mJ/cm$^2$) | 69 | 23 | 23 | 23 | 23 | 23 | 23 | 23 | 30 | 69 | 140 | 75 | 75 |
| Gloss | ○ | ○ | ○ | ○ | ○ | ○ | ○ | ○ | ○ | ○ | ○ | ○ | ○ |
| Smell | ○ | ○ | ○ | ○ | ○ | ○ | ○ | ○ | ○ | ○ | Δ | Δ | ○ |

Note:
*1 Compound 1: Triphenylsulfonium hexafluorophosphate
*2 Compound 2: Diphenyl-4-thiophenoxyphenylsulfonium hexafluorophosphate
*3 Compound 3: 4,4'-Bis[bis([-2-hydroxyethoxyphenyl)sulfonio]phenylsulfido bishexafluorophosphate
*4 Celloxide 2021: Alicyclic epoxy resin manufactured by Daicel Ltd.
*5 EHPE-3150: Alicyclic epoxy resin manufactured by Daicel Ltd.

TABLE 2

|  | Example |  |  |  |  |  |  |  |  |  | Comparative Example |  |  |
|---|---|---|---|---|---|---|---|---|---|---|---|---|---|
|  | 21 | 22 | 23 | 24 | 25 | 26 | 27 | 28 | 29 | 30 | 4 | 5 | 6 |
| Photopolymerization initiator: |  |  |  |  |  |  |  |  |  |  |  |  |  |
| obtained in Example 1 | 1.0 |  |  |  |  |  |  |  |  |  |  |  |  |
| obtained in Example 2 |  | 1.0 |  |  |  |  |  |  |  |  |  |  |  |
| obtained in Example 3 |  |  | 1.0 |  |  |  |  |  |  |  |  |  |  |
| obtained in Example 4 |  |  |  | 1.0 |  |  |  |  |  |  |  |  |  |
| obtained in Example 5 |  |  |  |  | 1.0 |  |  |  |  |  |  |  |  |
| obtained in Example 6 |  |  |  |  |  | 1.0 |  |  |  |  |  |  |  |
| obtained in Example 7 |  |  |  |  |  |  | 1.0 |  |  |  |  |  |  |
| obtained in Example 8 |  |  |  |  |  |  |  | 1.0 |  |  |  |  |  |
| obtained in Example 9 |  |  |  |  |  |  |  |  | 1.0 |  |  |  |  |
| obtained in Example 10 |  |  |  |  |  |  |  |  |  | 1.0 |  |  |  |
| Compound 1 |  |  |  |  |  |  |  |  |  |  |  |  | 1.0 |
| Compound 3 |  |  |  |  |  |  |  |  |  |  |  | 1.0 | 1.0 |
| Vinyl ether: |  |  |  |  |  |  |  |  |  |  |  |  |  |
| VEctomer 2010 (*6) |  |  | 25 | 25 | 25 | 25 | 25 | 25 |  | 25 |  | 25 | 25 |
| VEctomer 4020 (*7) | 60 | 60 | 25 | 25 | 25 | 25 | 25 | 25 | 60 | 25 | 60 | 25 | 25 |
| Triethylene glycol divinyl ether |  | 10 | 10 | 10 | 10 | 10 | 10 | 10 |  | 10 |  | 10 | 10 |
| Transparency | O | O | O | O | O | O | O | O | O | O | XX | X | O |
| Storage stability | O | O | O | O | O | O | O | O | O | O | O | O | O |
| Set to tough (mJ/cm²) | 23 | 12 | 12 | 12 | 12 | 12 | 12 | 12 | 12 | 23 | —(*8) | 24 | 34 |
| Gloss | O | O | O | O | O | O | O | O | O | O | — | X | O |
| Smell | O | O | O | O | O | O | O | O | O | O | — | O | Δ |

Note:
*6 VEctomer 2010: Aromatic urethane vinyl ether manufactured by Allied-Signal Co., Ltd.
*7 VEctomer 4020: Aliphatic ester vinyl ether having the following structural formula manufactured by Allied-Signal Co., Ltd.

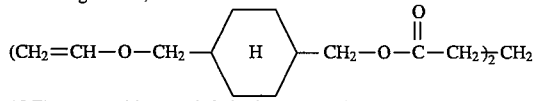

*8 The composition was inferior in compatibility of components and separated immediately after mixing and was not cured even by irradiation with more than 1000 mJ/cm² of ultraviolet ray.

As can be seen from the results of Tables 1 and 2, the compositions containing the photopolymerization initiator of the present invention are excellent in compatibility, transparency and curability and give a cured coat of excellent gloss, of less smell and of excellent adhesion to metal.

What is claimed is:

1. An energy ray-curable composition which contains a cation polymerizable substance and an onium salt represented by the following formula (1):

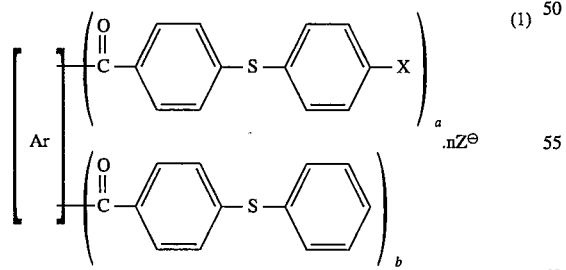

wherein Ar is

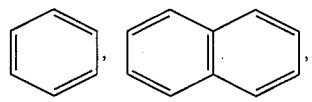

which may have at least one substituent selected from ($C_1$–$C_5$) alkyl group, ($C_1$–$C_5$) alkyloxycarbonyl group, ($C_1$–$C_5$) alkylcarbonyloxy group, benzoyl group, cyano group, ($C_1$–$C_5$) alkylthio group and halogen atom; X is a bisphenyl-sulfonio group represented by the following formula (2):

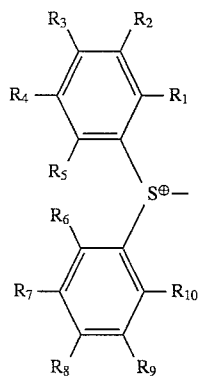

(2)

wherein $R_1$–$R_{10}$ each is a hydrogen atom, a halogen atom, a nitro group, an alkoxy group, an alkyl group, a phenyl group which may have a substituent of $C_6$–$C_{18}$, a phenoxy group, a phenylcarbonyl group, an alkylthio group, a phenylthio group, a benzyloxy group, a $C_1$–$C_{25}$ aliphatic group containing at least one hydroxyl group or a $C_3$–$C_{25}$ aliphatic group containing a group represented by the following formula:

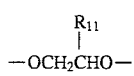

where $R_{11}$ is a hydrogen atom or an alkyl group; a is 1–4; b is 0 or 1–3; a+b is 1–4; n is 1–4; and Z is a halide represented by the following formula (3):

$$MQ_m\text{—}(OH)_l \qquad (3)$$

where M is a boron atom, a phosphorus atom, an arsenic atom or an antimony atom, Q is a halogen atom, m is 3–6, l is 0 or 1, and m+l is 4–6.

2. A composition according to claim 1 wherein the cation polymerizable substance is an epoxy compound, a vinyl ether compound or a cyclic ether compound.

3. A composition according to claim 2, wherein the epoxy compound is an alicyclic epoxy resin.

4. A composition according to claim 2, wherein the vinyl ether compound is triethylene glycol divinyl ether, tetraethylene glycol divinyl ether, cyclohexane-1,4-dimethyloldivinyl ether, 1,4-butanedioldivinyl ether,

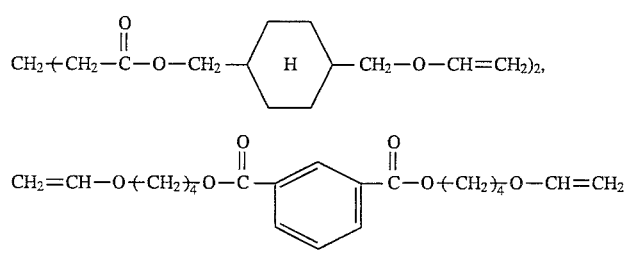

or urethane polyvinyl ether.

5. A composition according to claim 1, wherein the onium salt is represented by the following formula:

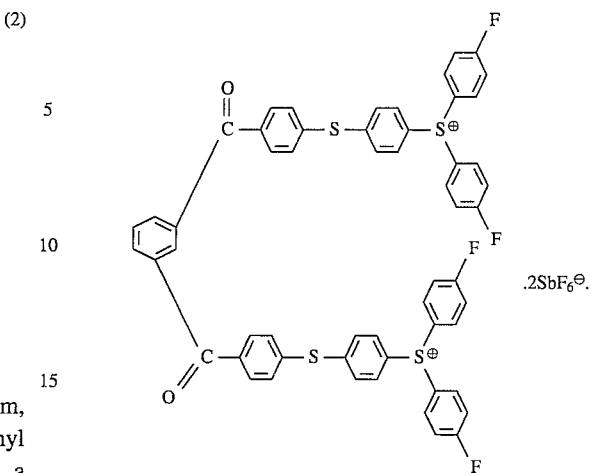

6. A composition according to claim 1, wherein the energy ray is an ultraviolet ray.

7. A composition according to claim 1 which comprises 100 parts by weight of the cation polymerizable substance and 0.01–20 parts by weight of the onium salt.

8. An ultraviolet ray-curable composition which comprises 100 parts by weight of an alicyclic epoxy resin and 0.1–10 parts by weight of the onium salt represented by the following formula:

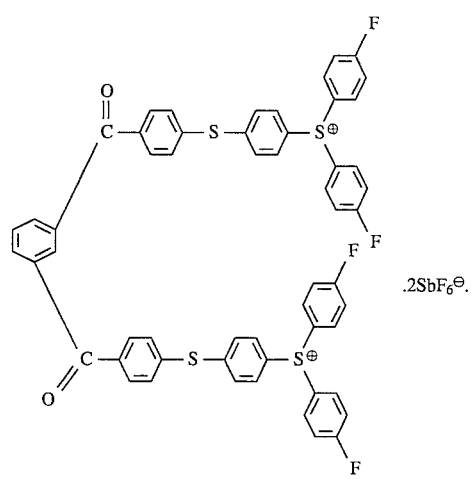

9. An ultraviolet ray-curable composition which comprises 100 parts by weight of a vinyl ether compound and 0.1–10 parts by weight of the onium salt represented by the following formula:

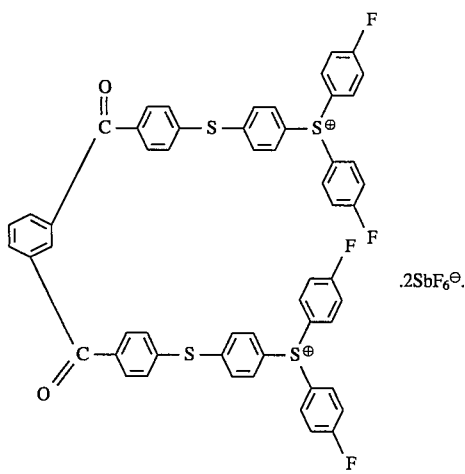

10. A composition according to claim 9, wherein the vinyl ether compound is triethylene glycol divinyl ether, tetraethylene glycol divinyl ether, cyclohexane-1,4-dimethyloldivinyl ether, 1,4-butanedioldivinyl ether,

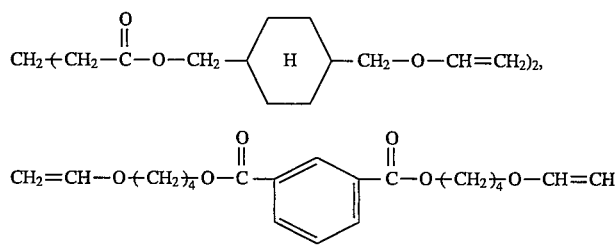

or urethane polyvinyl ether.

11. A composition according to claim 1, wherein the onium salt is represented by the following formula:

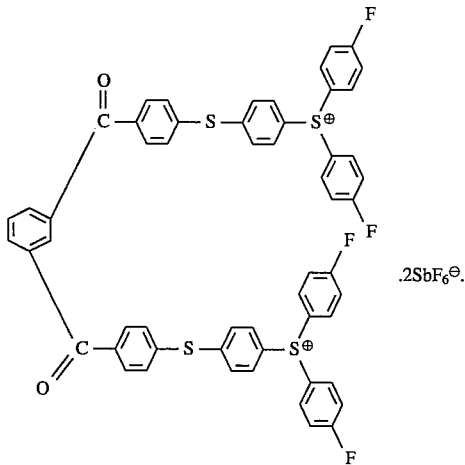

12. An ultraviolet ray-curable composition which comprises 100 parts by weight of an alicyclic epoxy resin and 0.1–10 parts by weight of the onium salt represented by the following formula:

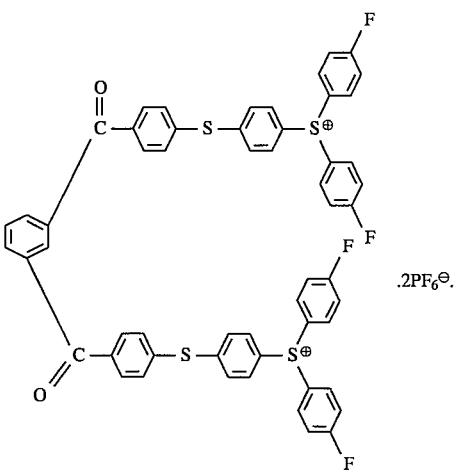

13. An ultraviolet ray-curable composition which comprises 100 parts by weight of a vinyl ether compound and 0. 1–10 parts by weight of the onium salt represented by the following formula:

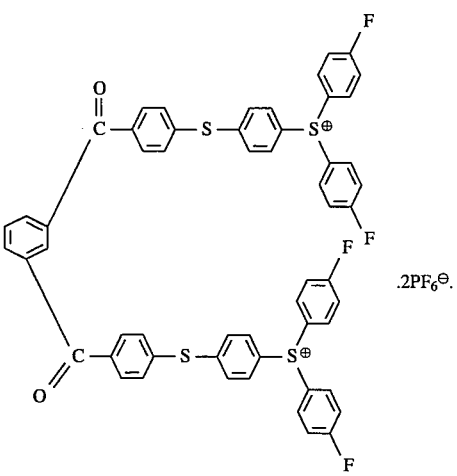

* * * * *

UNITED STATES PATENT AND TRADEMARK OFFICE
CERTIFICATE OF CORRECTION

PATENT NO.    : 5,502,083
DATED         : March 26, 1996
INVENTOR(S)   : Tetsuya Abe, Kazuhiko Ishii and Minoru Yokoshima It is certified that error appears in the above-identified patent and that said Letters Patent is hereby corrected as shown below:

Title page, item [56]

Foreign Application Priority Data should read

-- June 18, 1993    Japan . . . . . . 5-170853 --

Signed and Sealed this

Tenth Day of September, 1996

Attest:

BRUCE LEHMAN

Attesting Officer     Commissioner of Patents and Trademarks